US005439513A

United States Patent [19]

Periasamy et al.

[11] Patent Number: 5,439,513

[45] Date of Patent: Aug. 8, 1995

[54] DEVICE FOR FOCUSSING PARTICLES SUSPENDED IN A GAS STREAM

[75] Inventors: Ravindran Periasamy, Cary; David S. Ensor, Chapel Hill; Robert P. Donovan, Durham, all of N.C.

[73] Assignee: Research Triangle Institute, Research Triangle Park, N.C.

[21] Appl. No.: 251,643

[22] Filed: May 31, 1994

Related U.S. Application Data

[63] Continuation of Ser. No. 890,147, May 29, 1992, abandoned.

[51] Int. Cl.$^6$ .......... B03C 3/40

[52] U.S. Cl. .......... 96/25; 55/270; 55/DIG. 1; 95/78; 96/54; 96/60

[58] Field of Search .......... 96/25, 54, 60; 95/78, 95/80, 81; 209/127.1; 55/DIG. 1, 270; 364/502

[56] References Cited

U.S. PATENT DOCUMENTS

| | | | |
|---|---|---|---|
| 1,957,458 | 5/1934 | Horne et al. | 96/54 |
| 2,682,313 | 6/1954 | White | 95/80 |
| 3,040,497 | 6/1962 | Schwab | 96/54 X |
| 3,059,772 | 10/1962 | Le Baron | 209/127.1 |
| 3,496,701 | 2/1970 | Owe Berg | 55/6 |
| 3,561,253 | 2/1971 | Dorman | 73/24.03 |
| 3,827,217 | 8/1974 | Volsy | 55/121 |
| 3,853,750 | 12/1974 | Volsy | 55/4 X |
| 4,023,398 | 5/1977 | French et al. | 55/11 X |
| 4,209,306 | 6/1980 | Feldman et al. | 95/80 |
| 4,534,776 | 8/1985 | Mammel et al. | 55/136 |
| 4,734,105 | 3/1988 | Eliasson et al. | 55/5 |
| 4,737,268 | 4/1988 | Giddings | 209/127.1 X |
| 4,778,493 | 10/1988 | Fitch et al. | 55/136 |
| 4,976,749 | 12/1990 | Adamski et al. | 95/81 X |

OTHER PUBLICATIONS

Electrodynamic Balance Stability Characteristics and Applications to the Study of Aerocolloidal Particles by E. James Davis (A); Feb. 8, 1985; pp. 379–387.

Single Aerocolloidal Particle Instrumentation and Measurement by E. James Davis; Dept. of Chemical Engineering, University of Washington, Seattle, Wash. 98195; 7 pages, undated.

Davis (A), E. J. Electrodynamic Balance Stability Characteristics in Applications to the Study of Aerocoloidal Particles, Langmuir, 1:379–387 (1985).

Davis, E. J. and Ray, A. K., Single Aerosol Particle Size and Mass Measurements Using An Electrodynamic Balance, Journal of Colloid and Interface Science, vol. 75, No. 2, Jun. 1980.

Periasamy, R., Light Scattering and Transport Phenomena of Single Aerosols in the Micron and Submicron Range, Ph.D. dissertation, University of Mexico, Dec. 1982, pp. 28–44, 81–128, 137–147.

Davis, E. J., Transport Phenomena with Single Aerosol Particles, Aerosol Science and Technology, 2:121–144 (1983).

Davis, E. J., Electrodynamic Balance Stability Characteristics in Applications to the Study of Aerocoloidal Particles, Langmuir, 1:379–387 (1985).

*Primary Examiner*—Richard L. Chiesa

*Attorney, Agent, or Firm*—Oblon, Spivak, McClelland, Maier & Neustadt

[57] ABSTRACT

A device for controlling the motion of particles suspended in a gas stream is provided, including a pipe, through which at least a fraction of the gas stream flows, a source of AC voltage, a source of DC voltage, and a plurality of electrode sets positioned within the pipe in series, generating an inhomogeneous electric field to cause the particles suspended in the gas stream to concentrate into a narrow axial region in the center of the pipe. Each electrode set includes a first pair of opposed hyperboloidally shaped electrodes connected to the AC voltage source and a second pair of opposed hyperboloidally shaped electrodes connected to the DC voltage. The first and second pairs of opposed electrodes are positioned at spaced apart intervals around the circumference of the pipe to define an opening through which at least a fraction of the gas stream flows. The electrode sets are positioned within the pipe in series such that the gas stream flows through the openings defined by each successive electrode set. The spaced apart distance between the electrodes of each successive electrode set is decreased to reduce the size of the openings, causing the particles suspended in the gas stream to focus or concentrate along successively narrower axial regions in the center of the pipe.

39 Claims, 8 Drawing Sheets

DEVICE FOR FOCUSSING PARTICLES SUSPENDED IN A GAS STREAM

This application is a Continuation of application Ser. No. 07/890,147, filed on May 29, 1992, now abandoned.

BACKGROUND OF THE INVENTION

1. Field of the Invention

The present invention relates to a device and method for the control of the motion of particles suspended in a gas stream and, more particularly to a device and method for real-time, on-line sampling of particles in process gas streams.

2. Discussion of the Background

In a substantial number of industrial, manufacturing, and scientific processes, the detection, control and analysis of micron and submicron sized particulates is essential. Specifically, the removal of particles, detection of particles for particle counting, and/or sampling of particles for chemical analysis is often crucial to achieving maximum operating efficiency and to minimizing yield losses.

In the semiconductor industry, for example, particle contamination during VLSI manufacturing processes is one of the primary sources of yield loss. About 50% of all yield losses in semiconductor device fabrication are due to particles (i.e., contamination of wafers with particles). One source of particles during semiconductor device manufacture is vacuum processing equipment. This is due to the nature of the mechanical movements (e.g., wafer transfer) in the equipment, and chemical and physical deposition and etching processes which can form particles. Thus, semiconductor manufacturers require a device and method for the removal of particulate matter suspended in process gas streams that can also be utilized in a vacuum environment. Further, the device must have the capability of operating on gas streams having very low particle concentrations (e.g., 5 to 10 particles per cubic foot) and/or very high gas flow rates (e.g., 1 to 5 cubic feet per minute), which are characteristic of semiconductor process gas streams. Producers of specialty gases and researchers in aerosol science and technology represent others interested in particle contamination problems.

In addition to the actual removal of the particles that can potentially contaminate gases and the products being manufactured, sampling of particles present in gases and during product manufacturing provides an effective tool for evaluating the severity of particle contamination and probable yield loss, and for determining the likely source of the particles through particle analysis. In the case of sampling of particulate matter, it is highly desirable to perform such sampling on an unaltered gas/particle sample, during the actual manufacturing process (i.e., in real-time). Further, a sampling device that has the capability to be used on-line, with the processing equipment being operated, in both atmospheric and subatmospheric (i.e., vacuum) conditions, is also desirable.

Devices and methods have been developed for the removal and sampling of particulate matter suspended in gas streams in an attempt to minimize the presence of particles during processing and to isolate or capture particles for particle counting and analysis. Such attempts are characterized, generally, by providing (1) a means for aerodynamic focusing of the particles suspended in the gas stream or (2) a means for creating an electric field to apply a force on the suspended particles causing the particles to collect on a collecting plate or migrate to a designated area.

Available particle control and measurement devices and methods of the aerodynamic focusing type, such as Model HS-LAS Optical Particle Counter, manufactured by Particle Measuring Systems, Inc. of Boulder, Colo. are characterized by the use of an aerodynamic focusing inlet comprising (1) a sampling pipe having an inlet end, an outlet end, and a reduced diameter center portion, and (2) a sheath air inlet. The particle-enriched gas stream is introduced into the inlet end of the sampling pipe. After entering the reduced diameter center portion of the sampling pipe, the particle-enriched gas stream is surrounded by a sheath air stream, introduced through the sheath air inlet, flowing concentrically to the flow direction of the particle-enriched gas stream. The concentrically flowing sheath air stream causes the particles suspended in the particle-enriched gas stream to focus into a narrow axial region in the center of the sampling pipe. Once focused, the particles can be captured and removed, counted, or analyzed. Due to their reliance solely on aerodynamic forces to focus the suspended particles, devices and methods of the aerodynamic focusing type cannot effectively operate in subatmospheric conditions.

Many of the particle control devices and methods currently available utilize a means for creating an electric field to apply a force on particles in a gas stream to cause the particles to collect on a collecting plate or to migrate to a designated area. Such devices and methods are characterized by the use of a pair of electrodes connected to a direct current voltage supply for generating a uniform electric field. In such devices and methods, the particles are removed from the gas stream by (1) electrostatic charging in a unipolar manner of the particles, causing a migration of the charged particles to an oppositely charged electrode, and (2) removing the charged particles from the collecting electrode in a mechanical manner by rapping or vibrating the collecting electrode, such as, for example, in U.S. Pat. No. 3,827,217 to Volsy. Although such devices and methods are somewhat effective in separating the charged particles from the gas stream, the removal of the particles deposited on the collecting electrode by scraping, sweeping, rapping, or vibrating, causes a number of the particles already separated to become re-entrained into the gas stream. Further, due to the collection of the particles on the plate, and subsequent removal step, devices and methods of the collection/removal type do not provide an unaltered particle/gas sample and cannot be operated to perform real-time, on-line sampling for particle counting and analysis. In addition, such devices and methods are not effective for removing electrically neutral particles from the gas stream.

Other devices and methods utilizing a means for creating an electric field to apply a force on particles suspended in a gas stream are characterized by the use of a plurality of electrodes arranged in a specific configuration to drive the particles in the gas stream toward a particular area or region. For example, the device and method for the removal of particles from a gas stream by means of an electric field disclosed in U.S. Pat. No. 4,734,105 to Eliasson et al. includes an electrode configuration having step-wise decreasing electrode spacing between successive direct current field electrode pairs. An untreated gas stream loaded with particles enters the device through an inlet end and is ionized by the electrode pairs and electrically charged in a bipolar manner. A uniform electric field forces the charged particles progressively towards the center of the successive electrode pair configuration, wherein the gas stream loaded with particles is diverted off and withdrawn. Although such devices and methods provide improved particle removal relative to systems utilizing the collection/-removal process, their ability to effectively remove and accurately control the motion of particulate matter suspended in a gas stream is still problematic and extremely limited in application. Prior devices and methods cannot adequately transport the focused particles through the electric field or electrode configuration due to their reliance soley on aerodynamic forces (i.e., the velocity of the gas stream/particles flowing through the field), which forces are typically not present in vacuum conditions. Further, the electric field generated by a device of this type does not create sufficient force to focus the particles suspended in gas streams having very low particle concentrations and/or very high gas flow rates.

Other devices and methods for the removal of particulates in gas streams utilizing a plurality of electrodes arranged in a specific configuration attempt to provide greater control (i.e., focusing) of particle movement by a four electrode configuration connected to an alternating current voltage supply to generate a nonuniform, alternating electric field. U.S. Pat. No. 3,496,701 to Berg shows such an arrangement of four electrodes connected to an alternating current voltage supply. The non-uniform, alternating electric field generated includes a point of zero potential and zero electric field in the center of the configuration. The particulates suspended in the gas stream will concentrate at that point. Although such a system provides improved particle control and particulate focusing over the previously described devices and methods, the electric field generated by a Berg-type device lacks sufficient strength to focus the particles suspended in gas streams having very low particle concentrations and/or very high gas flow rates. In addition, a Berg-type system does not have the capability to operate in varying atmospheric conditions (i.e., atmospheric and subatmospheric) due to its reliance soley on aerodynamic forces (i.e., the velocity of the gas stream/particles flowing through the field) for particle transport and the lack of real-time AC voltage adjustment in response to changing pressures.

Notwithstanding the available devices and methods for particle control, there is a need for a particle control device and method that can operate in changing atmospheric conditions (i.e., atmospheric and subatmospheric), on gas streams having very low particle concentrations and/or very high gas flow rates, that can provide for particle removal, detection or analysis on-line, in real-time.

SUMMARY OF THE INVENTION

Accordingly, an important object of the present invention is to overcome the deficiencies of the prior art described above by providing a device and method for the control of the motion of particles suspended in a gas stream that can effectively operate in atmospheric and subatmospheric (i.e., vacuum) conditions.

Another key object of the invention is to provide a particle control device and method having the capability of effectively operating on gas streams having very low particle concentrations and/or very high gas flow rates.

Still another object of the present invention is to provide a particle control device and method that can be operated on-line and can provide for particle removal, detection or analysis in real-time.

Another object of the present invention is to eliminate reliance on aerodynamic forces for controlling the motion of the particles suspended in a gas stream for performing particle focusing and, in subatmospheric conditions, for performing particle transport.

Yet another object of the invention is to provide a particle control device and method having the capability of generating an electric field of sufficient strength to focus the particles suspended in gas streams having very low particle concentrations and/or very high gas flow rates.

Another object of the invention is to provide a device and method for controlling the motion of particles suspended in a gas stream by applying an inhomogeneous electric field generated from an AC field and a DC field to the gas stream.

Still another object of the invention is to provide a device and method for particle control including a plurality of electrodes, wherein at least two electrodes of the plurality of electrodes are connected to an AC voltage supplying means and at least two electrodes of the plurality of electrodes are connected to a DC voltage supplying means.

Another object of the invention is to provide a device and method for particle control including a plurality of electrode sets in series, each electrode set comprising a first pair of opposed electrodes connected to an AC voltage supplying means for oppositely charging the first pair of opposed electrodes and a second pair of opposed electrodes connected to a DC voltage supplying means for oppositely charging the second pair of opposed electrodes.

Yet another object of the invention is to provide a device and method for controlling the motion of particles suspended in a process gas stream, wherein the particles are electrically neutral.

These and other objects are achieved according to the present invention by providing a new and improved device and method for controlling the motion of particles suspended in a gas stream which includes a plurality of electrodes, positioned within a pipe, wherein at least two electrodes of the plurality of electrodes are connected to an AC voltage supply and at least two electrodes of the plurality of electrodes are connected to a DC voltage supply, for generating an inhomogeneous electric field to cause the particles suspended in the gas stream to concentrate into a narrow axial region in the center of the pipe.

In a preferred embodiment, the present invention provides a device and method for controlling the motion of particles suspended in a gas stream, including a pipe, through which at least a fraction of the gas stream flows, a source of AC voltage, a source of DC voltage, and a plurality of electrode sets positioned within the pipe in series. Each electrode set includes a first pair of opposed hyperboloidally shaped electrodes connected to the AC voltage source for oppositely charging the first pair of opposed electrodes and a second pair of opposed hyperboloidally shaped electrodes connected to the DC voltage source for oppositely charging the second pair of opposed electrodes. The first and second pairs of opposed electrodes are positioned at spaced apart intervals around the circumference of the pipe. The electrodes of the first pair of opposed electrodes are spaced apart a predetermined distance and disposed on a first axis in a plane, and the electrodes of the second pair of opposed electrodes are spaced apart at approximately the same predetermined distance and disposed on a second axis, which is perpendicular to the first axis and in approximately the same plane. The first and second pairs of opposed electrodes define an opening through which at least a fraction of the gas stream flows. The plurality of electrode sets are positioned within the pipe in series such that the gas stream flows through the openings defined by each successive electrode set. The spaced apart predetermined distance between the electrodes of the first and second pairs of electrodes of each successive electrode set is decreased to reduce the size of the openings defined by each successive electrode set causing the particles suspended in the gas stream to concentrate into successively narrower axial regions in the center of the pipe. A plurality of computer operated solenoid controlled valves for controlling the rate of flow of the gas stream through the pipe are positioned within the pipe. Each valve is positioned downstream from and adjacent to one of the openings defined by each successive electrode set. Each valve reciprocates between an open position, wherein the rate of flow of the gas stream through the pipe is generally unaffected, and a closed position, wherein the rate of flow is decreased. A plurality of computer operated switches controls the activation and deactivation of each of the electrode sets in response to the opening and closing of the valves.

Other desirable features of the present invention include (1) a particle charger, positioned upstream from the electrodes, for electrically charging the particles suspended in the gas stream and (2) a means, positioned downstream from the electrodes, for receiving the particles transported through the pipe and concentrated into the narrow axial region in the center of the pipe to perform particle detection or analysis.

Still other and more specific objects and features of the invention may be understood from an examination of the following description of the preferred embodiment of the drawings and invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
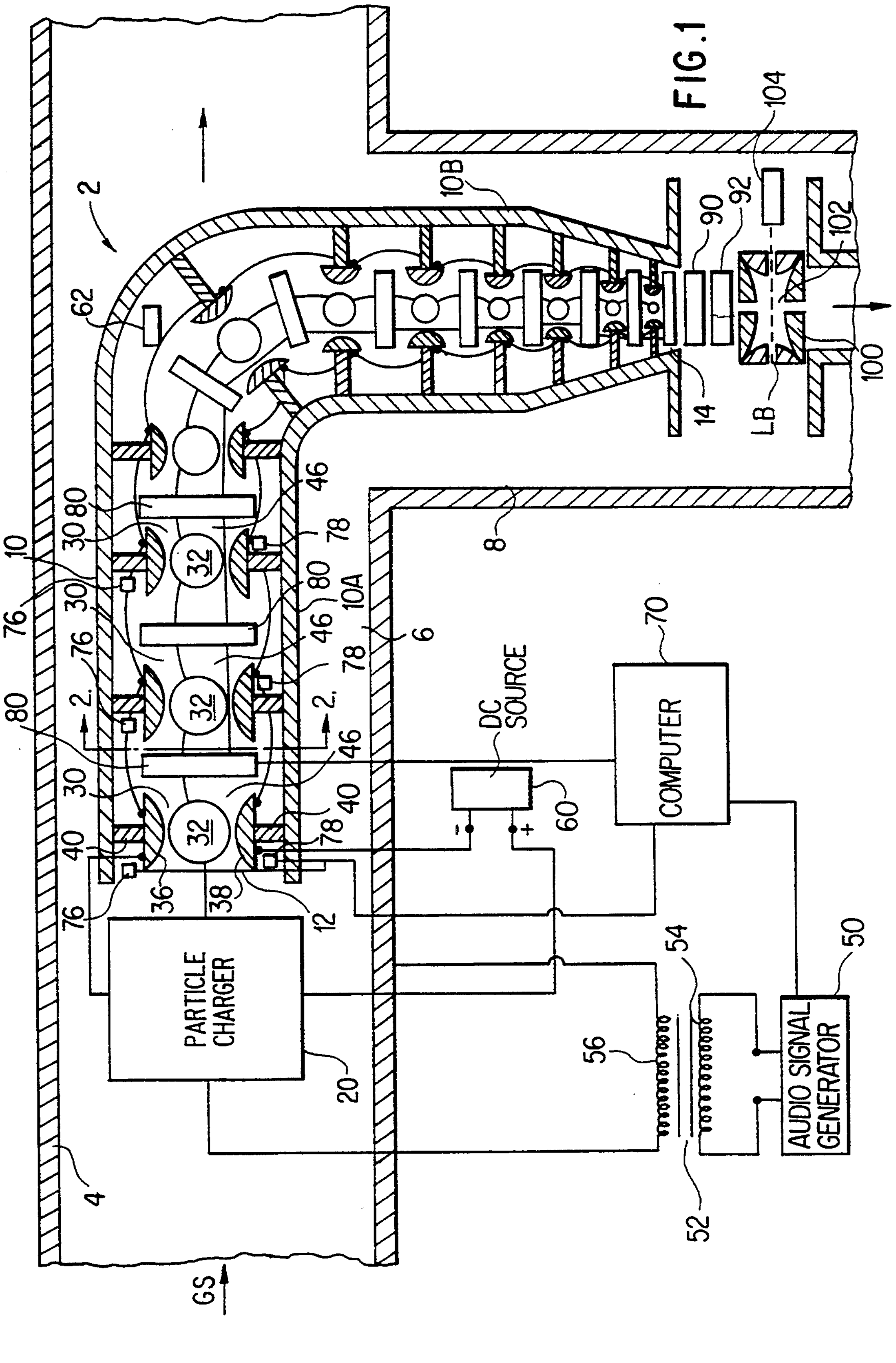
FIG. 1 is a side view, partly in cross-section, of a device for controlling the motion of particles in accordance with the preferred embodiment of the present invention.

Referring now to the drawings, wherein like reference numerals designate identical or corresponding parts throughout the several views, and more particularly to FIG. 1 thereof, there is shown a device 2 for controlling the motion of particles suspended in a gas stream GS. It is contemplated that the particle control device 2 of the present invention may be used for the removal or sampling of particles in the size range from 0.1 to 100 μm.

The particle control device 2 is positioned within a process gas line 4. The process gas line 4 includes a primary passage 6 and a secondary passage 8, branching off from the primary passage 6. The particle control device 2 comprises a sampling pipe 10, through which at least a fraction of the gas stream GS flows, having an inlet end 12 for receiving the incoming gas stream GS and an outlet end 14 through which the gas stream GS discharges. The particle control device 2 is positioned within the process gas line 4 such that a first portion 10A is positioned within the primary passage 6 and a second portion 10B is positioned within the secondary passage 8.

A particle charger 20, positioned upstream from the inlet end 12 of the sampling pipe 10, may be included for charging or enhancing the charge of the particles entering the sampling pipe 10. The particle charger 20 may be any type of particle charger, such as a radioactive source particle charger or an electrical source particle charger, such as are described in Electrostatics and its Applications, edited by A. D. Moore, John Wiley and Sons, N.Y. 1973, pages 57–85. While charging or enhancing the charge of the particles can improve particle focusing (i.e., the greater the charge on the particle, the more responsive the particle will be to the forces generated by the electric field), the particle control device 2 of the present invention has the capability to control the motion of both electrically charged and electrically neutral particles. The control of the motion of electrically charged and electrically neutral particles will be described in greater detail hereinafter with reference to FIG. 3.

Figure 2:
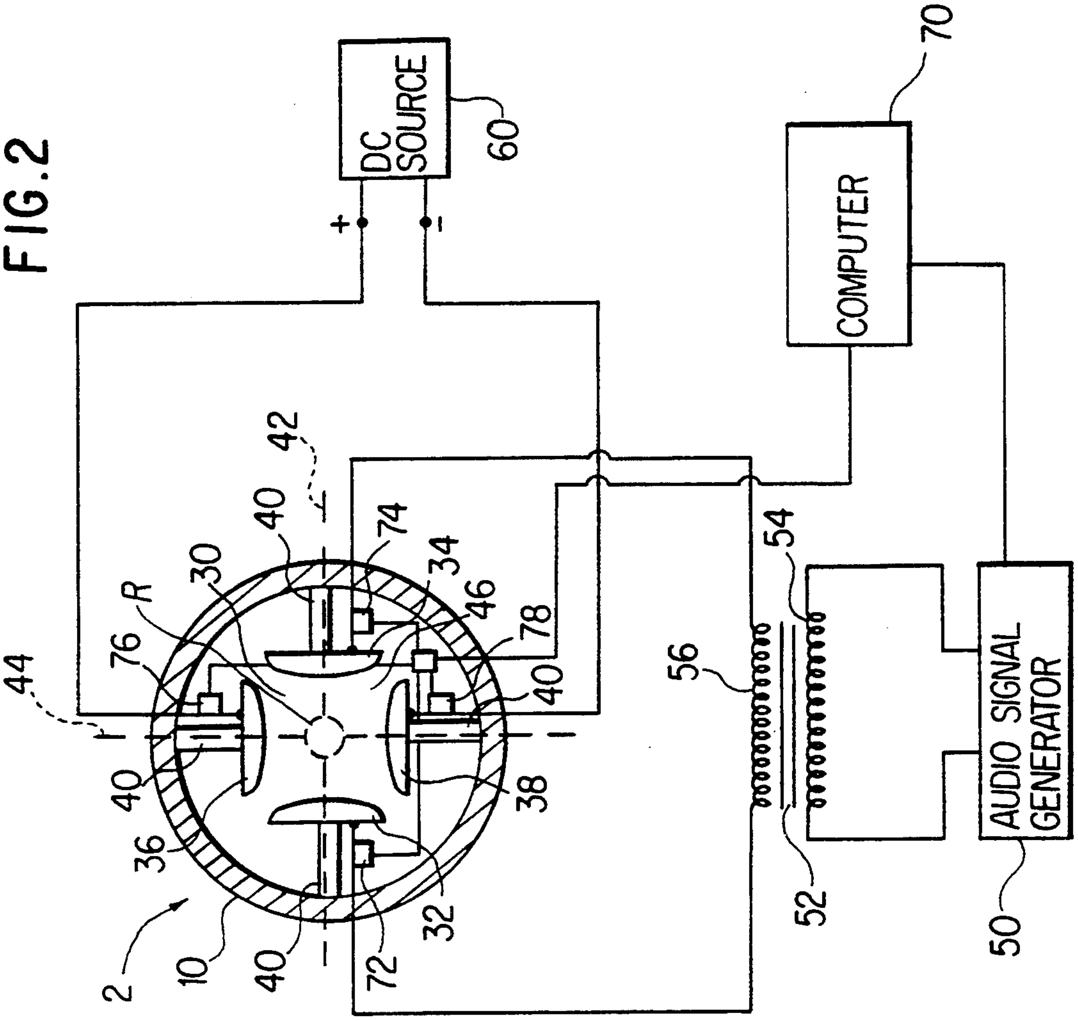
FIG. 2 is a cross sectional view, taken along line II—II in FIG. 1, showing an electrode set and the electrical circuitry and connections of the particle control device in accordance with the preferred embodiment of the present invention.

Positioned within the sampling pipe 10 are a plurality of electrode sets 30. Referring now to FIG. 2, each electrode set 30 comprises a first pair of opposed electrodes 32 and 34 and a second pair of opposed electrodes 36 and 38. The first pair of opposed electrodes 32 and 34 and second pair of opposed electrodes 36 and 38 are positioned within the sampling pipe 10 at spaced apart intervals around the circumference of the pipe 10. Each electrode 32, 34, 36, and 38 is hyperboloidally shaped and is mounted to the sampling pipe 10 by an insulating member 40.

The electrodes 32 and 34 of the first electrode pair are spaced apart a predetermined distance and disposed on a first axis 42. The electrodes 36 and 38 of the second electrode pair are spaced apart approximately at the same predetermined distance as the electrodes 32 and 34 and are disposed on a second axis 44. The first axis 42 and second axis 44 are perpendicular to one another and are approximately in the same plane. The first electrode pair 32 and 34 and the second electrode pair 36 and 38 define an opening 46 through which the gas stream GS flowing through the sampling pipe 10 flows.

The particle control device 2 includes an AC power source, which is audio signal generator 50, and a DC power source 60. A transformer 52, coupled to a primary 54 and secondary 56, is connected to the audio signal generator 50. Through the audio signal generator 50, the amplitude of the voltage and frequency can be varied. The audio signal generator 50 is connected to a computer 70, which controls the amplitude of the voltage and frequency output from the audio signal generator 50 in real-time, based on the pressure in the process gas line 4, as will be described hereinafter in greater detail with reference to FIGS. 6–9. The capability to control the amplitude of the voltage in real-time, in response to the changing pressure in the process gas line 4 (i.e., transition to and from atmospheric and subatmospheric conditions), enables the particle control device 2 of the present invention to effectively operate in both atmospheric and subatmospheric conditions. The need for an AC voltage adjustment feature will be explained more fully in the discussion of the operation of the particle control device 2.

A pressure gauge 62 is positioned within the sampling pipe 10 for measuring the pressure therein. The pressure gauge 62 is connected to the computer 70, which continually monitors the pressure within the sampling pipe 10 in order to determine if adjustment of the AC voltage is necessary. The pressure gauge 62 may be any type of pressure gauge, such as an electronic manometer, a vacuum gauge, or the like.

Referring to FIG. 2, a first switch 72 is connected to one end of the secondary 56 and a second switch 74 is connected to the other end of the secondary 56. The computer 70 is connected to the switches 72 and 74 and controls the opening and closing thereof. Electrode 32 is connected to switch 72 and electrode 34 is connected to switch 74 such that upon closing of the switches 72 and 74 the electrodes 32 and 34 will be oppositely charged.

Third and fourth switches 76 and 78 are connected to the DC source 60. The computer 70 is connected to the switches 76 and 78 and controls the opening and closing thereof. Electrode 36 is connected to the third switch 76 and electrode 38 is connected to the fourth switch 78 such that upon closing of the switches 76 and 78 the electrodes 36 and 38 will be oppositely charged. A positive charge is applied to electrode 36 and a negative charge is applied to electrode 38. Of course, the polarities of the electrodes 36 and 38 could be reversed.

Referring to FIG. 1, each of the electrodes 32 of the plurality of electrode sets 30 is connected to one end of the secondary 56 through a switch 72 in the manner described above. Each of the electrodes 34 of the plurality of electrode sets 30 is connected to the other end of the secondary 56 through a switch 74 in the manner described above. Each of the electrodes 36 and 38 of the plurality of electrode sets 30 are connected to the DC source 60 through switches 76 and 78, respectively, in the manner described above. The switches 72, 74, 76, and 78 provide the particle control device 2 of the present invention with the capability to selectively activate and deactivate an electrode set 30, enabling the particle control device 2 to operate effectively in subatmospheric conditions. In such conditions, aerodynamic forces are typically not present to transport the particles suspended in the gas stream through the sampling pipe 10. By selectively activating and deactivating adjacent electrode sets 30, as will be described in greater detail in the discussion of the operation of the particle control device 2, the particles suspended in the gas stream GS, which may have relatively little or no velocity in vacuum conditions, can be transported through the sampling pipe 10.

Each of the electrode sets 30 is positioned within the sampling pipe 10 such that the gas stream GS flows through the openings 46 defined by each successive electrode set 30. The spaced apart distance of the electrodes 32, 34, 36, and 38 of each successive electrode set 30 from the inlet end 12 to the outlet end 14 of the sampling pipe 10 is gradually decreased to reduce the size of the openings 46 defined by each successive electrode set 30. The gradual converging of the electrodes 32, 34, 36, and 38 causes the particles suspended in the gas stream GS to concentrate into successively narrower axial regions R in the center of the sampling pipe 10.

A plurality of solenoid controlled valves 80 are positioned within the sampling pipe 10 for controlling the rate of flow of the gas stream GS through the sampling pipe 10. Each valve 80 is positioned downstream from and adjacent to one of the openings 46 defined by each successive electrode set 30. Each valve 80 reciprocates between an open position, wherein the rate of flow of the gas stream GS is essentially unaffected, and a closed position, wherein the rate of flow of the gas stream GS is decreased. Each of the valves 80 is connected to the computer 70, which controls the synchronization and time interval $\Delta t$ of the opening and closing of the valves 80 such that the gas flow rate Q of the gas stream GS through the sampling pipe 10 is properly regulated. The control of the gas flow rate Q will be described in greater detail hereinafter with reference to FIGS. 6–9. The solenoid controlled valves 80 are preferably Series 9 high speed solenoid valves manufactured by General Valve Corporation located in Fairfield, N.J.

A particle counter 90 for measuring the concentration of the particles in the sampling pipe 10 is positioned within the secondary passage 8 of the process gas line 4 downstream from the outlet end 14 of the sampling pipe 10. The particle counter 90 may be any type of particle counter, such as a condensation nucleus counter or an optical particle counter, which are well known in the art. Also positioned downstream from the outlet end 14 of the sampling pipe 10 is a gas flow rate meter 92 for measuring the rate of flow of the gas stream GS flowing through the sampling pipe 10. The gas flow rate meter 92 is preferably a mass flow meter, such as the VFM series mass flow meter manufactured by Unit Instruments, Inc. located in Orange, Calif.

The particle counter 90 and gas flow rate meter 92 are connected to the computer 70, which controls the operation of various aspects of the particle control device 2. The particle concentration N, measured by the particle counter 90, and the gas flow rate Q, measured by the gas flow rate meter 92, are provided to the computer 70 for the purpose of setting various operating parameters of the particle control device 2 to control the time interval Δt and hence the gas flow rate Q of the gas stream GS as it flows through the sampling pipe 10. The computer control of the operation of various aspects of the particle control device 2 will be discussed in full detail hereinafter in the discussion of the operation of the particle control device 2 and, specifically, with reference to FIGS. 6–9.

A particle receiving device 100 is positioned downstream from the sampling pipe 10 adjacent to the outlet of the gas flow rate meter 92 for receiving the particles concentrated in the narrow axial region R in the center of the pipe 10. The particle receiving device 100 includes a chamber 102, wherein one particle can be suspended, contactless. A laser 104, which emits a fixed laser beam LB, is positioned so that the laser beam LB intercepts the particles received in the chamber 102. Preferably, the particle receiving device 100 is an electrodynamic balance, as is described and shown in Davis, E. J., Electrodynamic Balance Stability Characteristics and Applications to the Study of Aerocolloidal Particles, *Langmuir*, 1:379–387, 1985; Davis, E. J., Transport Phenomena with Single Aerosol Particles, *Aerosol Sci. Tech.*, 2(2):121–144, 1983; and Periasamy, R., Light Scattering and Transport Phenomena of single Aerosols in the Micron and Submicron Range, PhD Dissertation, University of New Mexico, December 1982.

Figure 3:
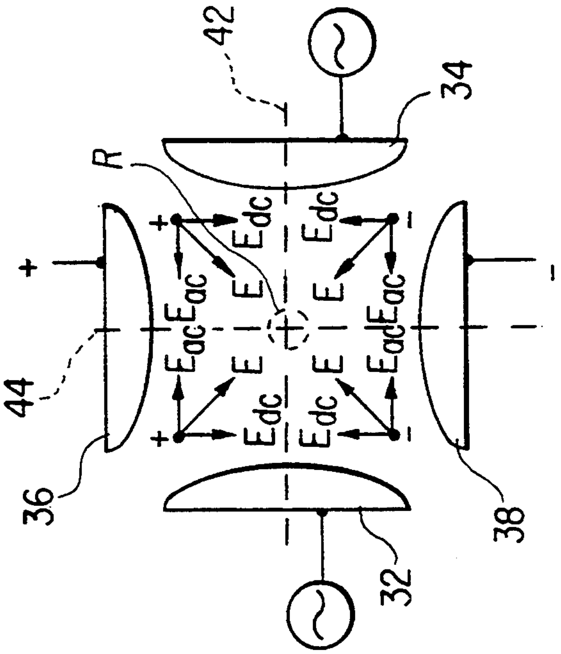
FIG. 3 is a schematic representation of the electrode and field configuration of the particle control device of the present invention.

The operation of the particle control device 2 of the preferred embodiment can best be understood by reference to FIG. 1, which shows the particle control device 2, FIG. 3, which is a schematic representation of the electrode and electric field configuration, and FIGS. 6–9, which are flow diagrams showing the routines for the computer control of the opening and closing of the solenoid controlled valves 80, the opening and closing of the switches 72, 74, 76, and 78 for the activation and deactivation of the electrode sets 30, and the adjustment of AC amplitude and frequency.

Figure 6:
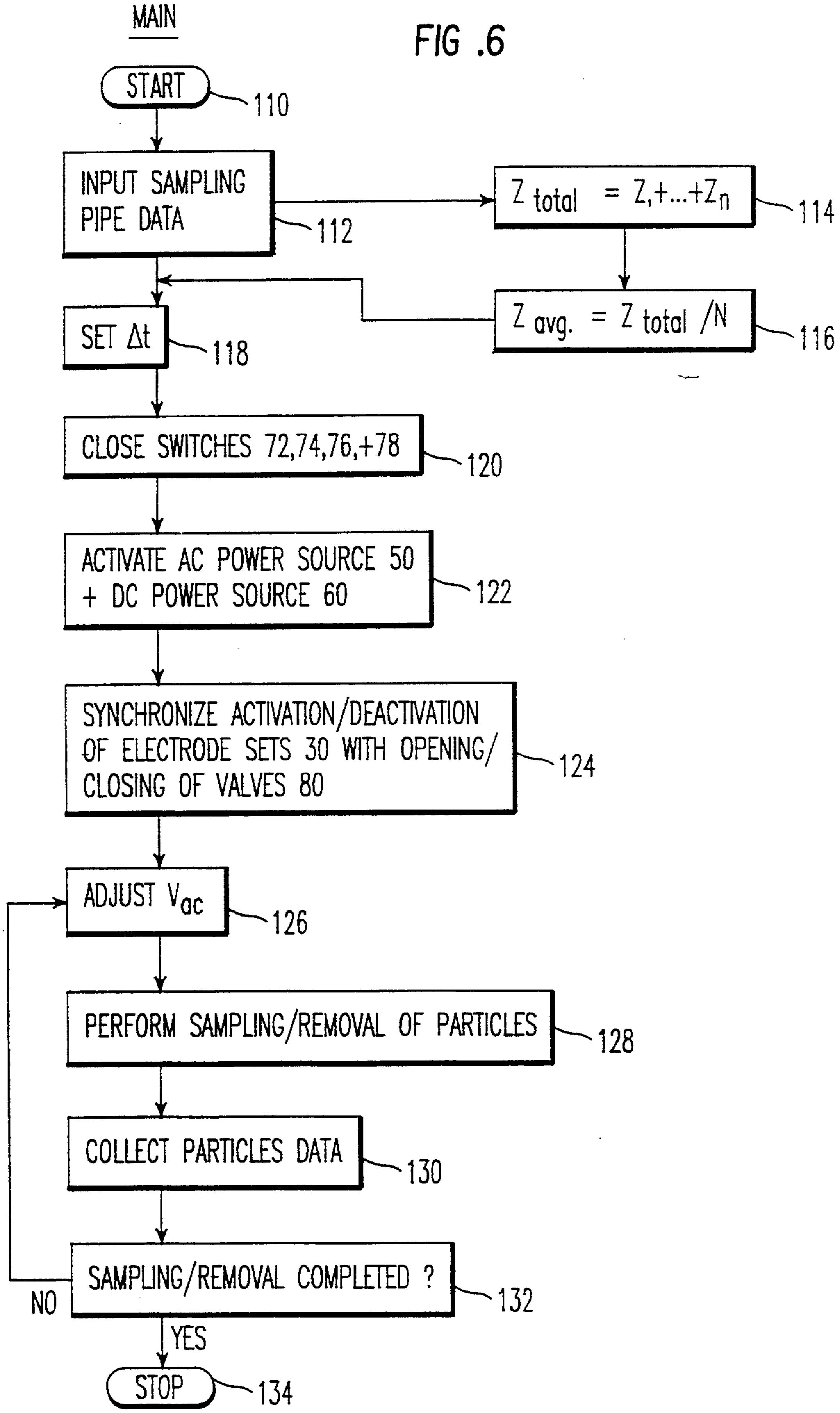
FIG. 6 is a flow diagram showing the main program for the computer control of the opening and closing of the solenoid controlled valves, the opening and closing of the switches for the activation and deactivation of the electrode sets, and the adjustment of the AC amplitude and frequency.
Figure 7:
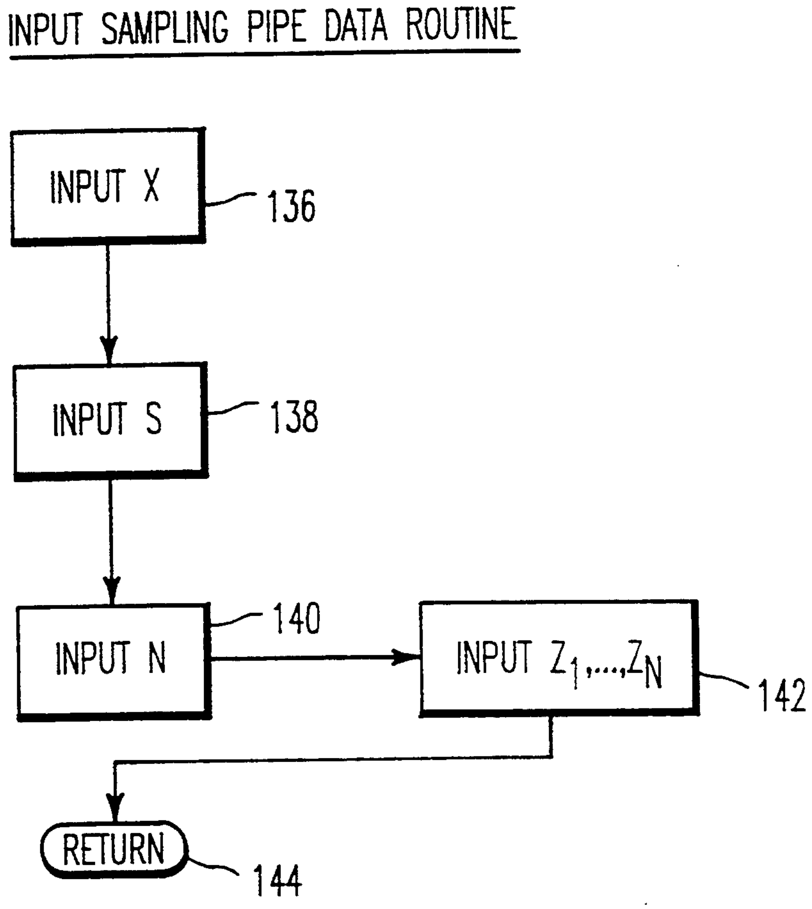
FIG. 7 is a flow diagram showing the subroutine which prompts the user for the input of data on the configuration of the sampling pipe.

Referring to FIG. 6, before initiating the removal and/or sampling of the particles suspended in the gas stream GS, the main program is started, step 110, and the computer 70 will prompt the user, step 112, to input data on the configuration of the sampling pipe 10. With reference to FIG. 7, which is a flow diagram showing the subroutine for the input of sampling pipe configuration data, the user is prompted to input the length X of the sampling pipe 10 at step 136, the cross-sectional area S of the sampling pipe 10 measured at the inlet end 12 at step 138, the number N of electrode sets 30 at step 140, and the spaced-apart distances $Z_1 \ldots Z_N$, depending on the number N of electrode sets 30, of the electrodes 32, 34, 36, and 38 of each successive electrode set 30 at step 142. This data is used to calculate various operating parameters to ensure the proper functioning of the particle control device 2 under varying pressure conditions, as will be discussed hereinafter with reference to FIGS. 8 and 9. The routine returns at step 144 to the main program.

Referring now to FIG. 6, after the sampling pipe input data (X, S, N and $Z_1 \ldots Z_N$) has been provided, the value for the average spaced-apart distance $Z_{Avg.}$ of the electrodes 32, 34, 36, and 38 of the electrodes sets 30 is calculated at steps 114 and 116. The sum $Z_{sum}$ of all the spaced-apart distances $Z_1$ to $Z_N$ is calculated at step 114. The average spaced-apart distance $Z_{Avg.}$ is calculated at step 116 by the equation $Z_{Avg.}=Z_{sum}/N$. The value $Z_{Avg.}$ is used to adjust the AC voltage $V_{AC}$ to the proper value, which will be described in detail hereinafter with reference to FIG. 9.

After calculating $Z_{Avg.}$, the process of initializing and setting various operating parameters is activated. The first operating parameter which is set is the time interval Δt, which represents the amount of time a valve 80 will remain in its open position, for the control of the rate of flow Q of the gas stream GS through the sampling pipe 10.

In order to achieve optimal results (i.e., remove/collect the maximum number of particles from the gas stream), the gas flow rate Q (cubic feet/minute—"CFM" or $cm^3$/sec.) within the sampling pipe 10 is controlled. Control of the gas flow rate Q in the sampling pipe 10 is necessary where the flow rate of the gas stream GS in the process gas line is very high, such as in the range of 1–5 CFM (471.7–2358.5 $cm^3$/sec.). In this range, at least a fraction of the particles suspended in the gas stream GS may not become focused in the narrow axial region R in the center of the sampling pipe 10. This is possible because the high gas flow rate Q will cause the particles suspended in the gas stream GS to travel through the sampling pipe 10 at a velocity which does not provide sufficient time for the forces generated by electric field to focus the particles.

To ensure that the maximum number of particles suspended in the gas stream GS become focused, the particle control device 2 includes the valves 80 for controlling the gas flow rate Q of the gas stream GS as it flows through the sampling pipe 10. The flow rate Q can be decreased by selectively opening and closing the computer operated solenoid controlled valves 80 for a time interval Δt. The time interval Δt, which represents the amount of time a valve 80 will remain in the open position, must be initialized and set in order to control the rate of flow Q of the gas stream GS through the sampling pipe 10. The equation for initially calculating the parameter Δt for a given sampling pipe configuration is:

$$\Delta t=[XS]/Q \quad (1)$$

where X is the length of the sampling pipe (cm), S is the cross-sectional area of the sampling pipe ($cm^2$), and Q is the gas flow rate ($cm^3$/sec.). This equation (1) is derived from two different equations for calculating the velocity V (cm/sec.) of the gas in the sampling pipe. The gas velocity V is given by the equation:

$$V=Q/S \quad (2)$$

where, as noted above, Q is the gas flow rate ($cm^3$/sec.) and S is the cross-sectional area of the sampling pipe ($cm^2$). The gas velocity V in the sampling pipe 10 can also be calculated from Δt by the equations $$V=X/\Delta t \quad (3$$

where, as noted above, X is the length of the sampling pipe (cm) and Δt is the time interval for the opening and closing of the valves 80. The equation (1) for calculating the time interval $\Delta t$ is derived from equations (2) and (3).

Figure 8:
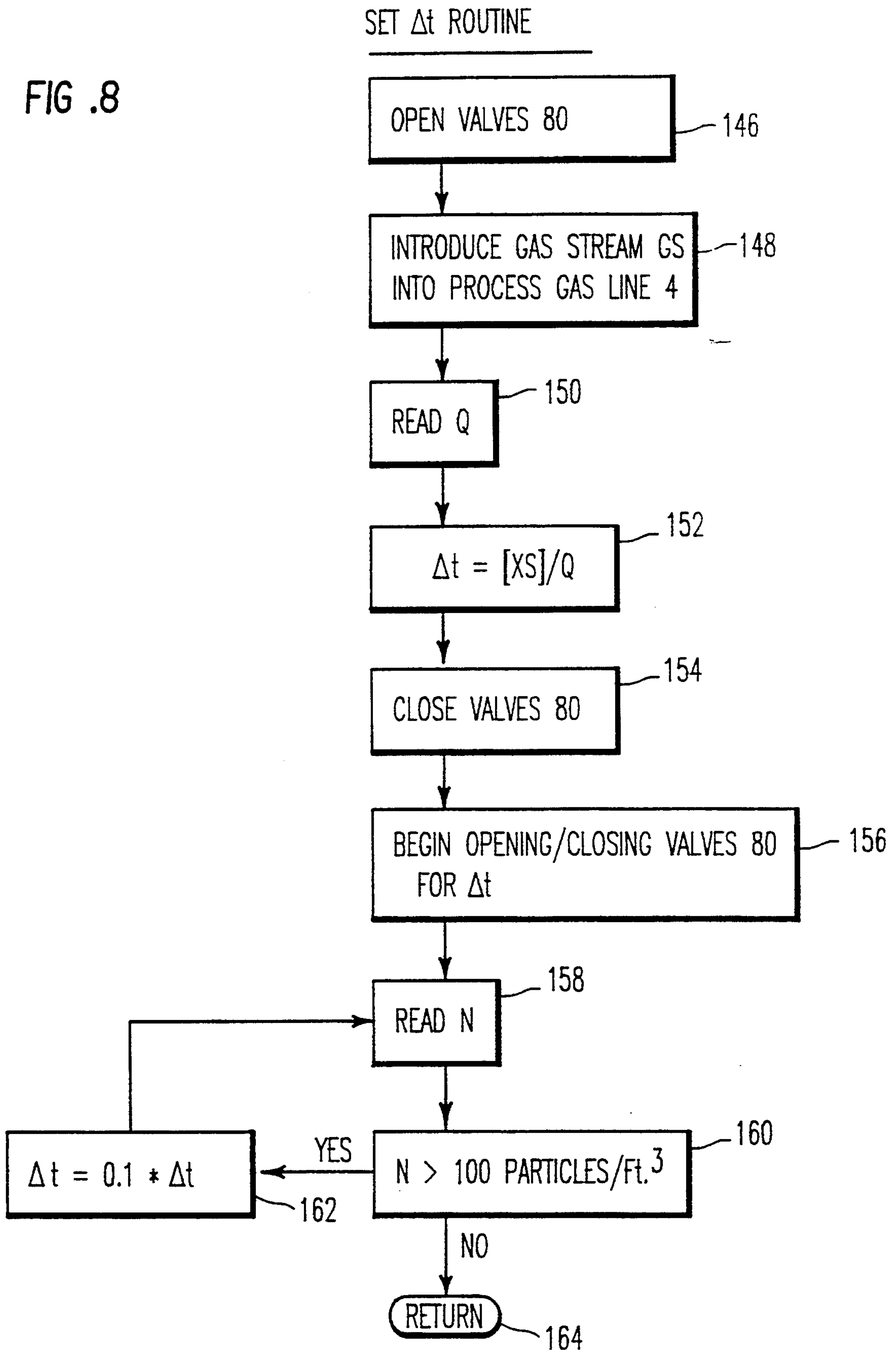
FIG. 8 is a flow diagram showing the subroutine for setting time interval $\Delta t$ for the opening and closing of the plurality of valves positioned in the sampling pipe.

Referring now to FIG. 8, each of the solenoid controlled valves 80, which are normally in the closed position, are activated at step 146 causing each of the valves 80 to reciprocate into the open position. Next, at step 148, a particle enriched gas stream GS is introduced into the process gas line 4 for the purpose of initializing and/or setting the operating parameters of the particle control device 2.

With reference to FIG. 1, the gas stream GS flows into the primary passage 6 of the process gas line 4. The gas stream GS will flow through the particle charger 20, which, if activated, will charge or enhance the particles passing therethrough. As discussed above, the inhomogeneous electric field generated in the particle control device 2 of the present invention has the capability to focus electrically neutral particles. Therefore, the particle charger 20 is not required and need not be included in the device 2.

Upon flowing through the particle charger 20, the gas stream GS will flow into the inlet end 12 of the sampling pipe 10. At this point, during the initialization of the operating parameters of the particle control device 2, the electrodes 32, 34, 36, and 38 of the electrode sets 30 are not charged and each of the solenoid-controlled valves 80 is in its opened position. The gas stream GS flows through the successive electrode sets 30 and valves 80 positioned in the sampling pipe 10 and through the outlet end 14 of the sampling pipe 10. Upon flowing out of the sampling pipe, the gas stream GS flows through the particle counter 90 and gas flow rate meter 92.

Referring now to FIG. 8, the computer 70, in step 150, instructs the gas flow rate meter 90 to measure the gas flow rate Q. The computer sets $\Delta t$, initially, in step 152, by calculating $\Delta t$ based on the equation $\Delta t = [XS]/Q$. After the initial value for $\Delta t$ has been calculated and $\Delta t$ set, the successive opening and closing of the valves 80 for the time interval $\Delta t$ is initiated.

All of the valves 80 are deactivated in step 154 causing the valves 80 to return to their closed positions. In step 156, the first valve 80 is activated, causing it to reciprocate to its open position for the time $\Delta t$ seconds. After the time interval $\Delta t$ has lapsed, the first valve 80 is deactivated, causing it to reciprocate to its closed position. Simultaneously with the closing of the first valve 80, the next successive valve 80 is activated, causing it to reciprocate to its open position for $\Delta t$ seconds. The opening and closing of successive valves 80 will continue as described above.

The initial calculated value for $\Delta t$ is adjusted based on the particle concentration N in the gas stream GS to ensure that the optimal number of particles suspended in the gas stream GS will be captured and/or removed. The gas flow rate Q in the sampling pipe 10 is directly proportional to the particle concentration in the gas stream GS—i.e., the lower the gas flow rate Q, the lower the particle concentration N. The particle control device 2 operates most efficiently when the particle concentration N in the gas stream GS as it flows through the sampling pipe 10 is less than or equal to 100 particles/$ft^3$. By adjusting the gas flow rate Q in the sampling pipe 10, the particle concentration N of the gas stream GS can be made to be less than or equal to 100 particles/$ft^3$. This is accomplished by adjusting $\Delta t$ to a lower value, causing each of the valves 80 to be open for a shorter period of time.

In step 158, the computer instructs the particle counter 22 to measure the particle concentration N (per $ft^3$) in the gas stream GS. In step 160, if the particle concentration $N > 100$ particles/$ft^3$, then $\Delta t$ is adjusted to a value of $\Delta t - 0.1^* \Delta t$, in step 162. As described above, decreasing the value of $\Delta t$ will shorten the amount of time each valve 80 is open, which will reduce the gas flow rate Q in the sampling pipe 10 and decrease the particle concentration N/$ft^3$.

The particle concentration N is continually measured, by returning to steps 158 and 160, and $\Delta t$ adjusted in step 162 until the reduction in the gas flow rate Q is sufficient to achieve the particle concentration $N \leqq 100$ particle/$ft^3$. Upon achieving the particle concentration $N \leqq 100$ particles/$ft^3$, the routine returns in step 164 to the main program.

Referring back to FIG. 6, with the optimal value for $\Delta t$ calculated, the switches 72, 74, 76, and 78 for each electrode set 30 are closed in step 120. The AC power source 50 and DC power source 60 are activated in step 122, charging the electrodes 32, 34, 36,and 38 of each of the electrode sets 30, which generates an inhomogeneous electric field. The directional forces E of the inhomogeneous electric field, and the directional forces $E_{AC}$ and $E_{DC}$ due to the AC and DC fields which form the inhomogeneous electric field, are illustrated in FIG. 3. In operation of the particle control device 2, the directional forces of the inhomogeneous electric field are of sufficient strength to balance the sum of the gravitational force and aerodynamic drag force, also acting on the suspended particles, to focus and maintain the particles suspended in the gas stream GS in the narrow axial region R in the center of the sampling pipe 2. The strength of the electric field (AC voltage and frequency and DC voltage) can be varied so that the particle control device 2 can focus particles of differing size having different charge-to-mass ratios.

Referring to FIG. 3, the forces $E_{AC}$, due to the AC field, and $E_{DC}$, due to the DC field, generate resultant forces E, causing the particles suspended in the gas stream GS to move into the narrow axial region R in the center of the sampling pipe 10. The resultant forces E will cause the electrically charged particles (i.e., positive and negative) and electrically neutral particles to move into the narrow axial region R. The neutral particles are caused to move by the polarization effects in the inhomogeneous electric field (i.e., dielectrophoresis). A known characteristic of inhomogeneous electric fields is their ability to act on neutral or uncharged matter. Under the influence of an inhomogeneous electric field, a neutral particle acquires, in effect, a negative charge on the side nearest the positive electrode and a positive charge on that side nearer the negative electrode. Since the particle is overall neutral, the two effective charges, positive and negative, are in fact equal. The externally applied inhomogeneous electric field diverges across the particle and produces unequal forces on the two effective charges. The net effect is an overall force on the neutral particle focussing them in the narrow axial region R between the electrodes. In the particle control device 2 of the present invention, the electrode configuration generates an inhomogeneous electric field which provides a force, on any particle in the region between the electrodes of FIG. 3 that is not yet in the narrow axial region R, that is directed towards the narrow axial region R in the center of the sampling pipe 10. As a result, the inhomogeneous electric field applied in the particle control device 2 causes both electrically charged and electrically neutral particles to move into the region R.

The inhomogeneous electric field of the present invention provides superior particle focusing and accurate particle control because of the unique combination of AC and DC electric fields and the hyperboloidal shape of the electrodes 32, 34, 36, and 38. The forces generated by the DC field $E_{DC}$ provide precise control of particle motion vertically, along the axis 44, while the forces generated by the AC field $E_{AC}$ provide precise control of particle motion horizontally, along the axis 42. The hyperboloidal shape of the electrodes 32, 34, 36, and 38 causes the electrical forces $E_{AC}$ and $E_{DC}$, and the resultant forces E, to be directed towards the center (i.e., axis) of the sampling pipe 10, creating the narrowest possible focusing region R (i.e., narrow axial region) in the center of the sampling pipe 10. The unique combination of AC and DC electric fields and the hyperboloidal shape of the electrodes 32, 34, 36, and 38, provides the particle control device 2 with the capability of effectively operating on gas streams having very low particle concentrations and/or very high gas flow rates.

The AC power source 50 operates, preferably, at an AC voltage from 500 to 5000 volts (peak to peak) and at a frequency from 20 to 200 cycles per second (Hz), depending upon the size of the particles being controlled and the pressure in the process gas line 4. For example, to provide optimal focusing of suspended particles at atmospheric pressure (76 cm mercury), wherein the particles are approximately 10 μm in size, an AC voltage of 2000 volts at a frequency of 60 cycles per second is preferable. The preferred DC voltage for operating the particle control device 2 ranges from 0 to 500 volts, depending on the size of the particles. To provide optimal focusing of particles 10 μm in size, a DC voltage of 200 volts is preferrable. For the voltage ranges described above, the preferred maximum spaced apart distance between the opposed electrodes 32 and 34 and between the opposed electrodes 36 and 38 is approximately 2.6 centimeters.

In varying conditions (i.e., transition to and from atmospheric and subatmospheric conditions), the AC voltage must be adjusted depending on the pressure. During the transition to and from atmospheric (76 cm mercury) and subatmospheric (0.01 cm mercury) conditions, the pressure in the process gas line is rapidly varying. As the gas in the process gas line is evacuated to create the vacuum condition or pumped in to return to ambient pressure, a corona discharge effect occurs during the pressure band from 1 cm mercury to 5 cm mercury. When the pressure in the process gas line is in this pressure band, the direction of the inhomogeneous electric field generated by the electrode sets 30 is altered. In order to account for this change, the AC voltage must be adjusted to a lower value.

The magnitude of the AC voltage adjustment is dependent upon the configuration of the sampling pipe 10 (i.e., the average spaced-apart distance $Z_{Avg.}$ of the electrodes 32, 34, 36, and 38 of the electrode sets 30; the shape of the electrodes; and the length X of the sampling pipe 10) and the pressure P in the sampling pipe 10. The AC voltage must be adjusted to a voltage so that the following equation is satisfied:

$$V_{AC}Z_{Avg.} \leqq V1 \qquad (4)$$

where $V_{AC}$ is the AC voltage, $Z_{Avg.}$ is the average spaced-apart distance between the electrodes 32, 34, 36, and 38 of the electrode sets 30, and V1 represents the threshold AC field strength (volts/cm). The value for V1 is calculated based on the equations $$V1 = A + (B * P) \qquad (5)$$

where A and B are geometric parameters that are determined for a given sampling pipe configuration, and P is the pressure (torr; 1 torr = 1 mm Hg) in the sampling pipe 10.

The constants A and B are determined experimentally for a given sampling pipe configuration. As discussed above, a corona discharge occurs during the pressure band from 1 cm mercury to 5 cm mercury. When the pressure in the process gas line is in this pressure band, the AC voltage breaks down causing the direction of the inhomogeneous electric field generated by the electrode sets 30 to be altered. A direct measurement of the threshold point (i.e., voltage) at which the AC voltage breaks down for a given pressure P due to the corona discharge can be made.

To determine the threshold AC voltage value, the AC voltage applied to the electrode sets 30 is increased gradually for various operating pressures P in the pressure band from 1 cm mercury to 5 cm mercury. The AC voltage is increased until the occurrence of the corona discharge, identified by a light blue glow emitted in the sampling pipe 10. The value of the AC voltage when the corona discharge occurs is the threshold AC voltage. By determining the threshold (i.e., break down) AC voltage value for various pressures, values for the constants A and B to be used in equation (5) can be determined for a given sampling pipe. For example, for hyperboloidally shaped electrodes separated by a maximum distance of 2.54 cm, the values of A and B were determined to be 60.4 volts/cm and 51.6 volts/cm-torr, respectively.

Figure 9:
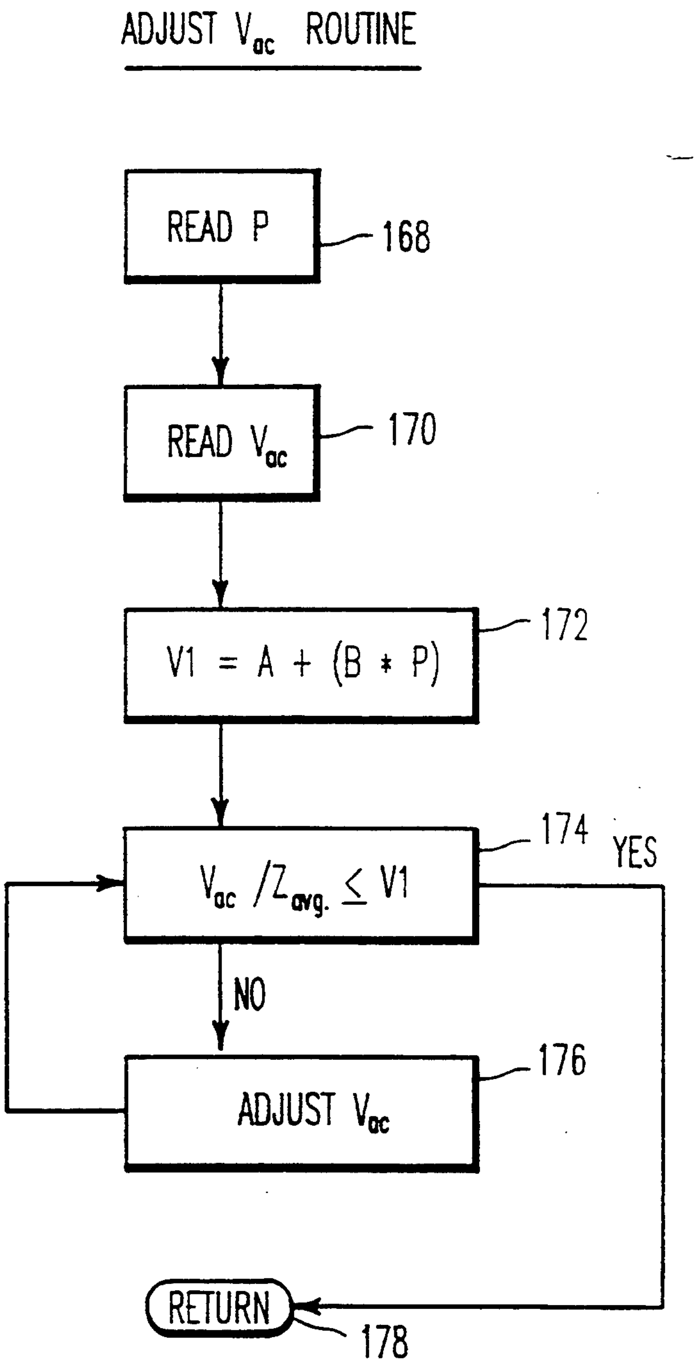
FIG. 9 is a flow diagram showing the subroutine for adjusting the AC voltage.

During the operation of the particle control device 2 of the present invention, the AC voltage is adjusted by the computer 70. Referring to FIG. 6, the computer executes the Adjust $V_{AC}$ routine in step 126. Referring now to FIG. 9, the computer, in step 168, instructs the pressure gauge 62 to measure the pressure within the sampling pipe 10. Next, in step 170, the computer sets $V_{AC}$ to the current AC voltage setting. In step 172, the computer calculates the value for V1, the threshold AC field strength (volts/cm), based on equation (5) described above, **V1=A+(B*P), wherein the values for the constants A and B are predetermined experimentally in accordance with the procedure described above. In step 174, the computer compares the value $V_{AC}/Z_{Avg.}$, where $Z_{Avg.}$ is the average spaced-apart distance between the electrodes 32, 34, 36, and 38 of the electrode sets 30, with V1 to determine if the AC voltage must be adjusted to a lower value in order to account for the change in direction of the inhomogeneous electric field. If $V_{AC}/Z_{Avg.}$ is less than or equal to V1, then $V_{AC}$ is already set to the appropriate value to account for any directional change in the electric field that occurs if the pressure in the sampling pipe 10 is in the range from 1 to 5 cm mercury (i.e., transition to or from subatmospheric conditions) and the routine routines to the main program in step 178. Conversely, if $V_{AC}/Z_{Avg.}$ is greater than V1, the computer in step 176 adjusts the AC voltage so that $V_{AC}/Z_{Avg.} \leqq$ V1. The subroutine illustrated in FIG. 9 is performed at predetermined time intervals throughout the sampling/removal procedure so that accurate particle control and focusing can be maintained as the pressure in the sampling pipe 10 varies. By providing a real-time, computer controlled AC voltage adjustment feature, the particle control device 2** can maintain accurate particle control and focusing and operate effectively in both atmospheric and subatmospheric conditions.

For operation of the particle control device 2 in subatmospheric conditions (i.e., in a vacuum), the gas stream GS may not have sufficient velocity to transport the suspended particles into the opening 46 of the first electrode set 30 or into successive openings 46 of successive electrode sets 30. The electric field generated by the first electrode set 30 will be sufficient to draw the particles suspended in the gas stream GS into the first opening 46 defined by the first electrode set 30 of the sampling pipe 10. Referring to FIG. 6, to ensure that the suspended particles will flow into the openings 46 defined by the successive electrode sets 30, in step 124, each electrode set 30 adjacent to and upstream from a valve 80 is deactivated simultaneously with the opening of the valve 80 for the same time interval Δt. The electric field generated by the next electrode set 30 in the series (adjacent to and downstream from the open valve 80) is sufficient to draw the suspended particles through the opening in the valve 80 and into the opening 46 defined by the next electrode set 30 in the series. By deactivating selected electrode sets 30 in conjunction with the opening of selected valves 80, the particle control device 2 of the present invention has the capability of operating in both atmospheric and subatmospheric conditions, wherein the gas stream GS may have a relatively low velocity or no velocity to transport the suspended particles through the particle control device 2. Reliance on aerodynamic forces for transporting particles through the particle control device 2 is eliminated.

Referring to FIG. 6, now that the values for the operating parameters have been set, the particle removal/-sampling process begins, in step 128. The gas stream GS and particles suspended therein are transported in the opening 46 defined by the first electrode set 30 by the velocity of the gas stream GS alone, or in combination with the force of the electric field generated by the first electrode set 30. Upon entering the opening 46, the inhomogeneous electric field generated from the AC field and DC field is applied to the particles suspended in the gas stream. As illustrated in FIG. 3 and discussed above, the electrical forces E will cause the particles suspended in the gas stream to move towards and concentrate in the narrow axial region R in the center of the sampling pipe 10.

If the gas stream GS has sufficient velocity, the gas stream GS, including the particles moving towards and concentrated in the narrow axial region R in the center of the sampling pipe 10, will continue to flow through the opening 46 of the first electrode set 30 and first valve 80 into the opening 46 of the next electrode set 30 in the series. The activation/deactivation of selected electrode sets 30 in synchronization with the opening/-closing of selected valves 80, as described above, ensures that the gas stream GS and particles suspended therein flow into the next opening 46. The computer 70 causes the switches 72, 74, 76, and 78 to open, deactivating the first electrode set 30 simultaneously with the opening of the valve 80 positioned downstream from and adjacent to the opening 46 of the first electrode set 30. As a result, the electric field generated by the next electrode set 30 in the series will draw the particles suspended in the opening 46 defined by the first electrode set 30, now deactivated, through the opened valve 80 into the opening 46 defined by the next electrode set 30 in the series. After Δt seconds has lapsed, the open valve 80 is deactivated, which causes it to reciprocate back to its closed position. Simultaneously with the closing of the valve 80, the computer 70 causes the switches 72, 74, 76, and 78 to close, activating the first electrode set 30. The simultaneous deactivation of an electrode set 30 and opening of the valve 80 downstream from and adjacent to that electrode set enables the forces of the electric field generated by the next electrode set 30 in the series, downstream from the opened valve 80, to draw the particles suspended in the gas stream GS through the opening 46 of the electrode set 30 and valve 80 into the opening of the next electrode set 30 in the series, either alone or in combination with the velocity of the gas stream GS.

The spaced-apart distance of the electrodes 32, 34, 36, and 38 of the next, successive electrode set 30 is slightly decreased, to reduce the opening 46 defined by the electrode set 30. As a result, the narrow axial region R in the center of the sampling pipe 10 is slightly decreased in size. The particles, therefore, will move into the narrower axial region R and become more concentrated and focused.

The gas stream GS and particles suspended therein will continue to flow through the openings 46 of successive electrode sets 30, wherein the inhomogeneous electric field is applied, and through successive valves 80 as described above. Upon flowing through the last opening 46 of the last successive electrode set 30 and adjacent valve 80, the particles suspended in the gas stream GS will be extremely concentrated and focused into a very narrow axial region R in the center of the sampling pipe 10. For example, at an AC voltage of 4,000 volts peak-to-peak, operating at a frequency of 60 Hz, and a DC voltage of 200 volts, within a 2.54 cm sampling pipe, particles of approximately 14 μm in size were focused into a narrow axial region R having a diameter of approximately 1.5 mm. The gas stream GS and concentrated particles are discharged through the outlet end 14 of the sampling pipe 10.

The particles are discharged through the particle counter 90 and gas flow meter 92 into the chamber 102 of the particle receiving device 100. Once in the chamber 102 of the particle receiving device 100, which is preferably an electrodynamic balance, particle data is collected in step 130. Each particle can be detected by intercepting the laser beam LB emitted from the laser 104 for counting the number of particles removed from the gas stream GS or suspended contactless in the chamber 102 for real-time, on-line analysis, such as measuring the particle's mass, charge, size, and optical spectra. After the particle in the chamber 102 is interrogated, the particle can be ejected or vaporized by, for example, exposure to an intense IR laser beam (not shown). In step 132, the computer prompts the user to determine if the sampling/removal process is complete. If the process has been completed, the computer will stop execution in step 134. If the sampling/removal process is to be continued, the computer returns to step 126 to adjust the AC voltage $V_{AC}$.

Figure 4:
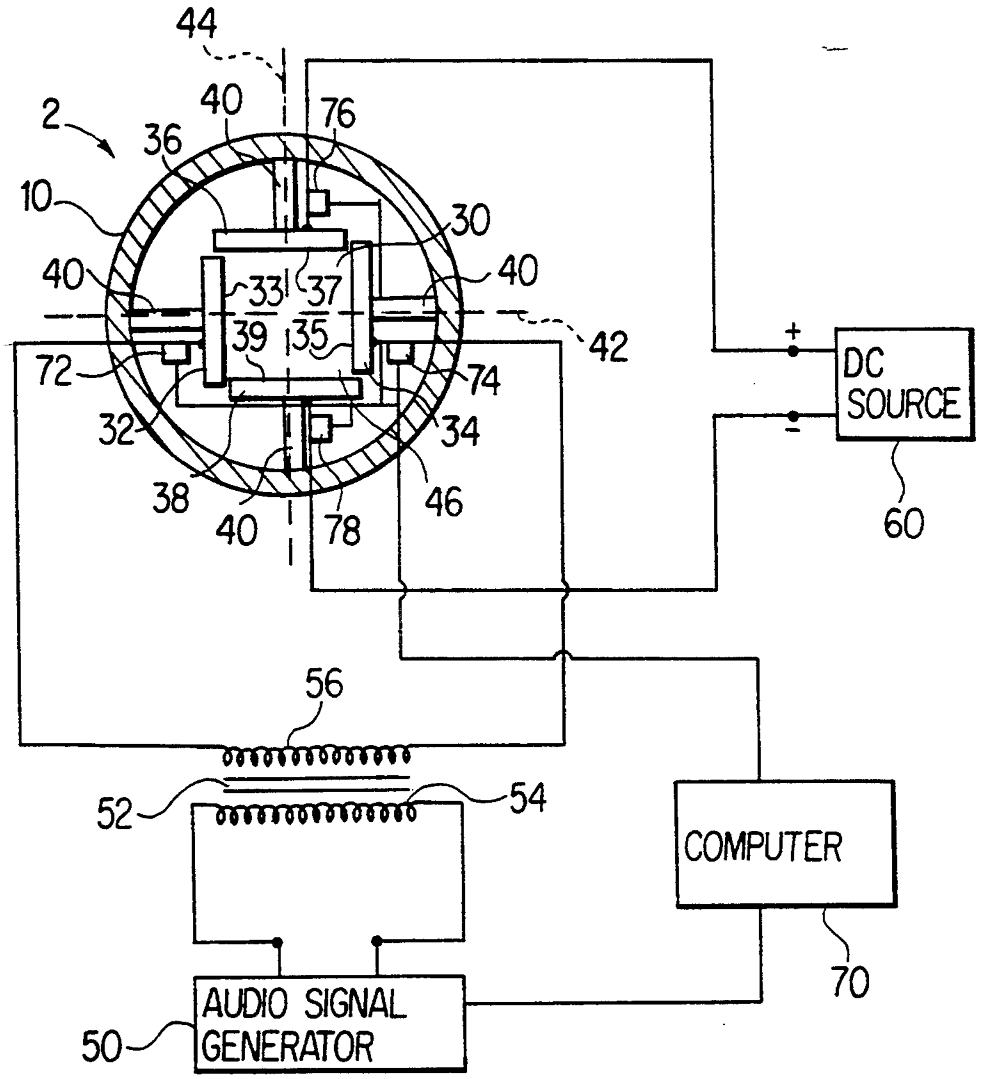
FIG. 4 is a cross sectional view showing (1) an electrode set, wherein the opposed surfaces of the electrodes are flat in shape, and (2) the electrical circuitry and connections of the particle control device of the present invention.
Figure 5:
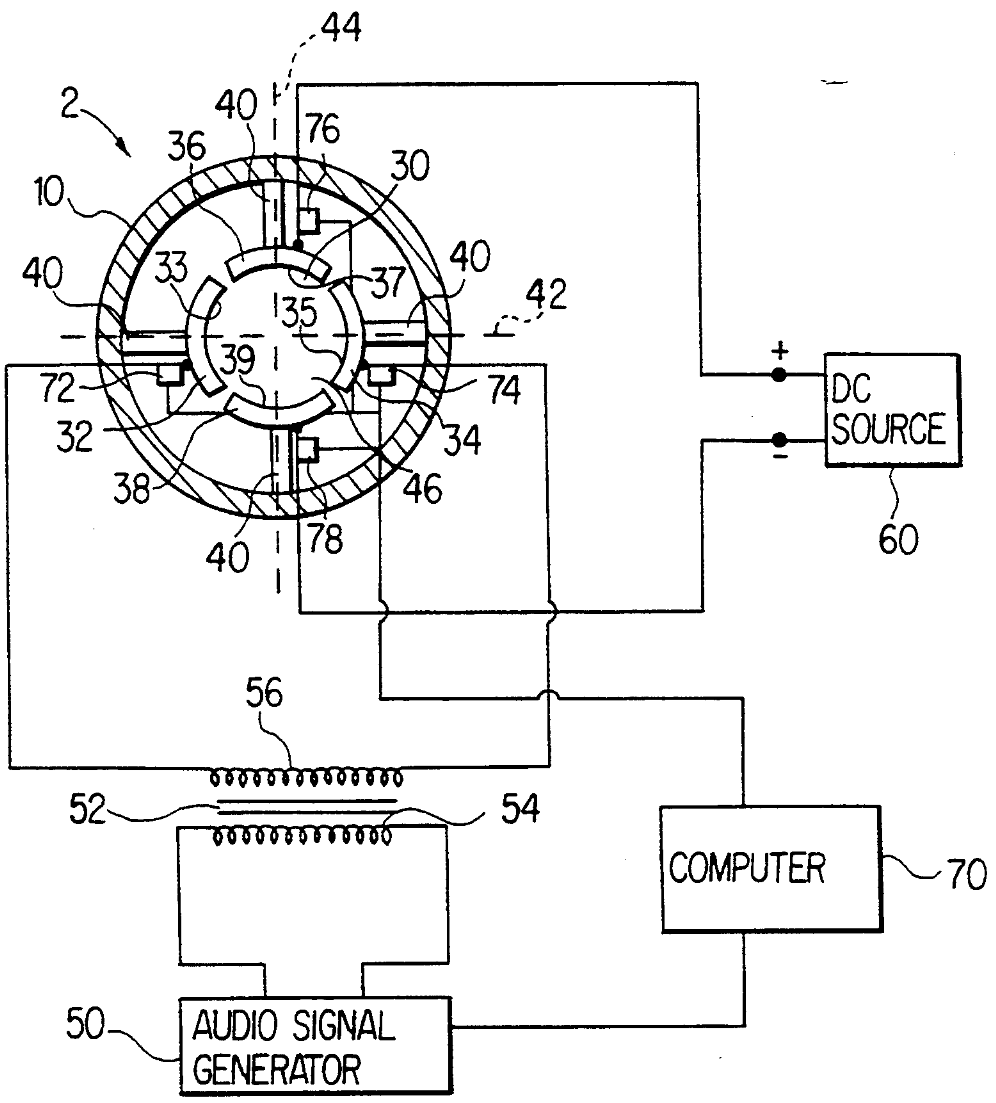
FIG. 5 is a cross sectional view showing (1) an electrode set, wherein the opposed surfaces of the electrodes are arcuate in shape, and (2) the electrical circuitry and connections of the particle control device of the present invention.

Referring to FIG. 4, an alternate embodiment of the present invention is shown, wherein the electrodes 32, 34, 36, and 38 are rectangular in shape and have flat opposed surfaces 33, 35, 37, and 39. Referring to FIG. 5, a third embodiment of the present invention is shown, wherein the electrodes 32, 34, 36, and 38 are rectangular in shape and have arcuate opposed surfaces 33, 35, 37, and 39. While the hyperboloidal shape is preferred, the electric field generated by the flat and arcuate shaped electrode geometries creates a sufficient electrical force to cause the particles suspended in the gas stream GS to focus into a narrow axial region R in the center of the sampling pipe 10.

The particle control device 2 of the present invention is designed to operate directly within process gas lines of vacuum processing equipment. The capability to operate on-line is extremely important because it allows an unaltered particle/gas sample to be captured in real-time to perform removal, detection or analysis in real-time. Performing these operations in real-time facilitates the obtaining of reliable particle data and evaluation of potential contamination situations as rapidly as possible.

Obviously, numerous (additional) modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A device for focussing particles that are suspended in an axial region of a gas stream along a narrow axial region that is contained in said axial region of said gas stream, comprising:

a pipe, enclosing the axial region of the gas stream and through which at least a fraction of the gas stream flows, having an inlet end for receiving said fraction of the gas stream and an outlet end for expelling said fraction of the gas stream after said gas stream has traversed said pipe;

means for supplying an AC voltage having an amplitude and a frequency;

means for supplying a DC voltage; and field generating means, positioned within said pipe but outside of said axial region, for generating an inhomogeneous electric field within said pipe for focussing charged and uncharged particles suspended in said axial region of said gas stream into said narrow axial region of said gas stream, said field generating means including a plurality of electrodes that are each positioned outside of said axial region of said gas stream, wherein a first pair of opposed AC electrodes of said plurality of electrodes are connected to opposite polarity terminals of said AC voltage supplying means and oppose one another across said axial region, a first pair of opposed DC electrodes of said plurality of electrodes are connected to opposite polarity terminals of said DC voltage supplying means and oppose one another across said axial region, wherein a time average force that is induced in response to electric fields generated by a combination of a DC voltage applied across said first pair of opposed DC electrodes and an AC voltage applied across said first pair of opposed AC electrodes, on any charged or uncharged particle that is located in any portion of said axial region that is outside of said narrow axial region, is directed toward said narrow axial region, thereby focussing all particles in said axial region into said narrow axial region;

wherein said first and second pairs of opposed electrodes are positioned at spaced apart intervals around the circumference of said pipe;

wherein the electrodes of said first pair of opposed electrodes are spaced apart a predetermined distance and positioned on a first axis in a plane, and the electrodes of said second pair of opposed electrodes are spaced apart at substantially the same predetermined distance and positioned on a second axis, said second axis is perpendicular to said first axis and in substantially the same plane, said first and second pairs of opposed electrodes defining an electrode set and an opening through which at least a fraction of said gas stream flows; and wherein said field generating means includes a plurality of said electrode sets positioned within said pipe in series, such that the gas stream flows through the openings defined by each successive electrode set.

2. A device according to claim 1, wherein distances between the electrodes of the first and second pairs of opposed electrodes of each successive electrode set are decreased to reduce the size of the openings defined by each successive electrode set causing the particles suspended in the gas stream to concentrate into successively narrower axial regions in the center of said pipe.

3. A device according to claim 2, wherein said plurality of electrode sets extends approximately from the inlet end to the outlet end of said pipe.

4. A device according to claim 1, further comprising:

means, positioned downstream from said field generating means, for receiving the particles that have been concentrated in the narrow axial region in the center of the pipe.

5. A device according to claim 4, wherein said particle receiving means comprises:

means for detecting the number of particles received.

6. A device according to claim 5, wherein said particle detecting means comprises:

a laser for emitting a fixed laser beam to intercept said received particles.

7. A device according to claim 4, wherein said particle receiving means comprises:

a chamber; and means for suspending one of the received particles contactless in said chamber.

8. A device according to claim 7, wherein said suspending means comprises an electrodynamic balance.

9. A device according to claim 1, wherein at least one electrode of said plurality of electrodes of hyperboloidal shape.

10. A device according to claim 1, wherein said first pair of opposed electrodes includes a first pair of opposed surfaces and said second pair of opposed electrodes includes a second pair of opposed surfaces, said first and second pairs of opposed surfaces being arcuate in shape.

11. A device according to claim 1, wherein said first pair of opposed electrodes includes a first pair of opposed surfaces and said second pair of opposed electrodes includes a second pair of opposed surfaces, said first and second pairs of opposed surfaces being flat in shape.

12. A device according to claim 1, wherein the amplitude of said AC voltage supplying means ranges from 500 to 5,000 volts.

13. A device according to claim 12, wherein the frequency of said AC voltage supplying means ranges from 20 to 200 Hz.

14. A device according to claim 13, wherein the voltage of said DC voltage supplying means ranges from 0 to 500 volts.

15. A device according to claim 1, wherein the spaced apart predetermined distance between the electrodes of the first and second pairs of electrodes is approximately 2.6 centimeters or less.

16. A device according to claim 1, further comprising:

means, positioned within said pipe downstream and adjacent at least one of said openings, for controlling a rate of flow of the gas stream based on the number of particles suspended in the gas stream.

17. A device according to claim 16, wherein said flow rate control means comprises a valve reciprocating between a closed position, wherein the gas stream and the particles suspended in the gas stream are prevented from flowing through said valve, and an open position, wherein the gas stream and the particles suspended in the gas stream are permitted to flow through said valve.

18. A device according to claim 17, wherein said valve is solenoid controlled.

19. A device according to claim 18, wherein the reciprocating of said valve between said closed position and said open position is computer controlled.

20. A device according to claim 17, wherein said flow rate control means comprises a plurality of said valves downstream and adjacent each one of said openings defined by each successive electrode set.

21. A device according to claim 20, further comprising:

switching means for selectively deactivating each electrode set for transporting the particles suspended in the gas stream through the openings defined by each successive electrode set.

22. A device according to claim 21, wherein the selective deactivation of each electrode set by said switching means is computer controlled.

23. A device according to claim 22, wherein the deactivation of selected electrode sets is synchronized with the reciprocation of said valves such that selected electrode sets upstream and adjacent opened valves are deactivated.

24. A device according to claim 1, further comprising:

means, connected to said AC voltage supplying means, for varying the amplitude and the frequency.

25. A device according to claim 24, wherein said varying means is computer controlled.

26. A device according to claim 24, wherein said varying means comprises an audio signal generator coupled to a variable transformer.

27. A device according to claim 1, further comprising:

means, positioned upstream from said field generating means, for charging the particles suspended in the gas stream.

28. A device according to claim 1, further comprising:

means for counting the number of particles suspended in the gas stream.

29. A device according to claim 1, further comprising:

means for measuring a flow rate of the gas stream.

30. A device according to claim 1, further comprising:

means for measuring the pressure within said pipe.

31. A device for controlling the motion of particles suspended in a gas stream, comprising:

a pipe, through which at least a fraction of the gas stream flows, having an inlet end for receiving said fraction of the gas stream and an outlet end for expelling said fraction of the gas stream;

means for supplying an AC voltage having an amplitude and a frequency;

means for supplying a DC voltage;

means, coupled to the means for supplying an AC voltage and to the means for supplying a DC voltage and positioned within said pipe, for generating an inhomogeneous electric field for focussing the particles suspended in the gas stream so they concentrate into a narrow axial region in the center of the pipe while they remain suspended in the gas stream, wherein the means for generating is located outside of the narrow axial region;

said means for generating comprising a plurality of electrodes, including a first set of electrodes and a second set of electrodes, the first set of electrodes is located outside of a first region of the narrow axial region, the second set of electrodes is located outside of a second region of the narrow axial region that is separate from and spaced downstream of the first region;

wherein the first set of electrodes are disposed around the first region of the narrow axial region and define a first diameter of the narrow axial region along the first region; and wherein the second set of electrodes are disposed around the second region of the narrow axial region and define a second diameter of the axial region which is less than the first diameter of the narrow axial region, thereby resulting in focussing of a set of particles suspended in the gas stream that is flowing consecutively past the first set of electrodes and then past the second set of electrodes.

32. A device according to claim 31, further comprising:

means, positioned within said pipe, for controlling a rate of flow of the gas stream based on the number of particles suspended in the gas stream.

33. A device for controlling the motion of particles suspended in a gas stream, comprising:

a pipe, through which at least a fraction of the gas stream flows, having an inlet end for receiving said fraction of the gas stream and an outlet end for expelling said fraction of the gas stream;

means for supplying an AC voltage having an amplitude and a frequency;

means for supplying a DC voltage;

means, coupled to the means for supplying an AC voltage and to the means for supplying a DC voltage, for generating an inhomogeneous electric field for focussing the particles suspended in the gas stream by generating a force upon the particles urging the particles into a narrow axial region in the center of the pipe while remaining suspended in the gas stream, wherein the means for generating is entirely located outside of the narrow axial region;

wherein said means for generating comprises a plurality of electrodes, including a first set of electrodes and a second set of electrodes, the first set of electrodes is located along a first region of the narrow axial region, the second set of electrodes is located along a second region of the narrow axial region that is separate from and spaced downstream of the first region;

wherein the first set of electrodes are disposed around the narrow axial region and define a first diameter of the narrow axial region along the first region; and wherein the second set of electrodes are disposed around the narrow axial region and define a second diameter of the narrow axial region along the second region, thereby resulting in further focussing of a set of particles suspended in the gas stream that is flowing consecutively past the first set of electrodes and then past the second set of electrodes.

34. A device according to claim 33, further comprising:

switching means, coupled to said means for generating, for selectively activating and deactivating said means for generating in order to transport the particles suspended in the gas stream through the pipe.

35. A device for focussing particles from an axial region that is aligned with a direction of flow of a gas stream in which the particles are suspended into a narrow axial region that is contained in said axial region, comprising:

a pipe having an axis, an inlet end for receiving the gas stream, and an outlet end for expelling the gas stream, the axial region being aligned along said axis of said pipe and inside of said pipe;

AC voltage generating means for generating an AC voltage;

DC voltage generating means for generating a DC voltage;

field generating means, positioned within said pipe, for generating an inhomogeneous electric field within said axial region that is aligned along the axis of the pipe such that said inhomogeneous electric field generates a force upon any particle that is within the axial region but outside of the narrow axial region urging said any particle toward the narrow axial region, said field generating means including a plurality of electrodes all of which are located outside of said narrow axial region, wherein at least a first two AC electrodes of said plurality of electrodes are connected to opposite polarity terminals of said AC voltage generating means and oppose one another across a first segment of said axial region and at least a first two DC electrodes of said plurality of electrodes are connected to opposite polarity terminals of said DC voltage generating means and oppose one another across a second segment of said axial region;

wherein at least a second two AC electrodes of said plurality of electrodes are structured for connection to opposite polarity terminals of said AC voltage generating means and oppose one another across a second segment of said axial region and at least a second two DC electrodes of said plurality of electrodes are structured for connection to opposite polarity terminals of said DC voltage generating means and oppose one another across said second segment of said narrow axial region, said second segment of said narrow axial region is separate from and spaced downstream of said first segment;

wherein a portion of the narrow axial region inside said first segment of said narrow axial region has a first diameter which is larger than a second diameter of a portion of said narrow axial region that is inside said second segment.

36. A device for focussing particles that are suspended in an axial region of a flowing gas stream into a narrow axial region that is aligned with and contained in said axial region, comprising:

a pipe having an axis, an inlet end for receiving the gas stream, and an outlet end for expelling the gas stream, said axial region and said narrow axial region being within the pipe and aligned with said axis;

means for focussing charged and uncharged particles that are inside said axial region and outside of said narrow axial region into said narrow axial region, comprising means for generating an inhomogeneous electric field at every point that is inside of said axial region, said inhomogeneous electric field having an AC component and a DC component in a focussing region that is inside of said axial region and outside of said narrow axial region, such that at for any particle at any point in the focussing region said inhomogeneous electric field induces forces upon said any particle such that a time average of said forces urges said any particle from the focussing region towards said narrow axial region, whereby all particles in said axial region are focussed into said narrow axial region;

said means for focusing comprises a plurality of electrodes, including a first set of electrodes and a second set of electrodes, the first set of electrodes is located along a first segment of the axial region, the second set of electrodes is located along a second segment of the axial region that is separate from and spaced downstream of the first segment;

wherein the first set of electrodes are disposed around the axial region and define a first diameter of the axial region along the first segment; and wherein the second set of electrodes are disposed around the axial region and define a second diameter of the axial region along the second segment, thereby resulting in a further focusing of a set of particles suspended in the gas stream that is flowing consecutively past the first set of electrodes and then past the second set of electrodes.

37. A device according to claim 36, wherein each set of the first and second sets of electrodes comprises a first pair of electrodes and a second pair of electrodes.

38. A device according to claim 37, wherein:

said means for generating further comprises an AC power supply, said AC power supply being connected to the first pair of electrodes to provide alternating electric power across the first pair of electrodes, thereby providing said AC component, and wherein said means for generating further comprises a DC power supply, said DC power supply being connected to the second pair of electrodes to provide DC electric power across the second pair of electrodes, thereby providing said DC component.

39. A device according to claim 38, wherein the first pair of electrodes oppose one another across said axial region and the second pair of electrodes oppose one another across said axial region.

* * * * *